(12) United States Patent
Licht et al.

(10) Patent No.: US 10,604,500 B2
(45) Date of Patent: Mar. 31, 2020

(54) COMPOUNDS HAVING TWO OR MORE EXOVINYLENE CYCLOCARBONATE UNITS

(71) Applicant: BASF SE, Ludwigshafen am Rhein (DE)

(72) Inventors: Ulrike Licht, Ludwigshafen (DE); Viktoria Leonhardt, Ludwigshafen (DE); Verena Mormul, Ludwigshafen (DE); Karl-Heinz Schumacher, Ludwigshafen (DE); Gabor Boerzsoenyi, Ubstadt-Weiher (DE); Rainer Klopsch, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/335,153

(22) PCT Filed: Sep. 11, 2017

(86) PCT No.: PCT/EP2017/072767
§ 371 (c)(1),
(2) Date: Mar. 20, 2019

(87) PCT Pub. No.: WO2018/054713
PCT Pub. Date: Mar. 29, 2018

(65) Prior Publication Data
US 2019/0241538 A1    Aug. 8, 2019

(30) Foreign Application Priority Data
Sep. 21, 2016  (EP) .................. 16189808

(51) Int. Cl.
*C07D 317/38*  (2006.01)
*C08G 64/02*   (2006.01)
*C09D 169/00*  (2006.01)

(52) U.S. Cl.
CPC ....... *C07D 317/38* (2013.01); *C08G 64/0241* (2013.01); *C09D 169/00* (2013.01)

(58) Field of Classification Search
CPC .... C08F 222/20; C08F 224/00; C08F 220/08; C08F 220/18; C08F 220/28; C08F 226/00; C08F 2220/283; C08F 2220/1825; C08F 8/32; B32B 27/00; B32B 27/08; B32B 27/32; B32B 27/36; B32B 37/12; B32B 7/00; B32B 7/12; B32B 2037/1269; C08G 71/04; C08G 4/00; C08G 65/34; C08G 2650/44; C08G 2650/50; C09D 135/02; C09D 11/107; C09J 135/00; C09J 135/02; C09J 11/06; C09J 11/08; C09J 201/06; C08K 5/17; C08K 5/06; C08K 5/053; C08K 5/0025; C08L 59/00; C08L 71/12; C09K 3/1006

See application file for complete search history.

(56) References Cited

U.S. PATENT DOCUMENTS

| | | | |
|---|---|---|---|
| 3,541,087 A | 11/1970 | Tedeschi et al. | |
| 2016/0186008 A1 | 6/2016 | Klopsch et al. | |
| 2017/0096408 A1 | 4/2017 | Gibanel et al. | |
| 2018/0155479 A1* | 6/2018 | Licht ................ | B32B 7/12 |

FOREIGN PATENT DOCUMENTS

| | | | | |
|---|---|---|---|---|
| DE |   1 064 938 |   9/1959 | | |
| DE |   1 176 358 |   8/1964 | | |
| DE | 26 39 083 A1 |   3/1978 | | |
| DE | 27 37 951 A1 |   3/1979 | | |
| EP |   0 622 378 A1 | 11/1994 | | |
| EP |   3 286 173 |   2/2018 | | |
| EP |   3 310 866 |   4/2018 | | |
| WO | WO 2011/089089 A1 |   7/2011 | | |
| WO | WO 2011/157671 A1 | 12/2011 | | |
| WO | WO 2012/175427 A2 | 12/2012 | | |
| WO | WO 2012/175431 A2 | 12/2012 | | |
| WO | WO 2013/144299 A1 | 10/2013 | | |
| WO | WO 2015/010924 A1 |   1/2015 | | |
| WO | WO 2015/039807 A1 |   3/2015 | | |
| WO | WO 2015/164692 A1 | 10/2015 | | |
| WO | WO 2015/164703 A1 | 10/2015 | | |
| WO | WO-2015164703 A1 * | 10/2015 | ........... | C09D 179/02 |
| WO | WO 2016/169858 A1 | 10/2016 | | |
| WO | WO 2016/202652 A1 | 12/2016 | | |
| WO | WO-2016202652 A1 * | 12/2016 | ............... | B32B 7/12 |

OTHER PUBLICATIONS

International Search Report dated Nov. 6, 2017 in PCT/EP2017/072767 filed Sep. 11, 2017.

* cited by examiner

*Primary Examiner* — Christopher M Rodd
(74) *Attorney, Agent, or Firm* — Oblon, McClelland, Maier & Neustadt, L.L.P.

(57) ABSTRACT

What are described are compounds having two or more exovinylene cyclocarbonate units, wherein the exovinylene cyclocarbonate units are bonded to one another via at least one organic, siloxane-free connecting group which is not bonded directly to the exovinylene double bonds, excluding connecting groups formed by polymerization of (meth) acrylic monomers. The connecting group preferably has at least one acetal group. Also described are a process for preparing the compounds, two-component binders comprising the compounds, and uses of the compounds.

18 Claims, No Drawings

COMPOUNDS HAVING TWO OR MORE EXOVINYLENE CYCLOCARBONATE UNITS

The invention relates to compounds having two or more exovinylene cyclocarbonate units, wherein the exovinylene cyclocarbonate units are connected to one another via at least one organic, siloxane-free connecting group which is not bonded directly to the exovinylene double bonds, excluding connecting groups formed by polymerization of (meth)acrylic monomers. Also described are a process for preparing the compounds, two-component binders comprising the compounds and uses of the compounds.

Coating compositions used are frequently two-component systems in which isocyanate components react with polyol components to give a polyurethane polymer of high molecular weight. These systems are applied either as solvent-free and anhydrous reactive neat systems or as a coating composition dissolved in an organic solvent. The coating compositions are applied to a first substrate by means of a suitable application system and then curing is effected, optionally after evaporation of the solvent. The reactive isocyanates present in conventional coating compositions constitute a toxicological risk. This relates firstly to the processing of these coating compositions in the use thereof, because the isocyanates generally have high toxicity and high allergenic potential. There is secondly the risk that, in the case of flexible substrates, aromatic isocyanate that has not fully reacted will migrate through the substrate and will be hydrolyzed there by fractions of water to give carcinogenic aromatic amines. What are therefore desirable are isocyanate-free two-component systems for curable coating compositions with good curing properties, if at all possible even at room temperature.

WO 2011/157671 discloses a cyclocarbonate compound having a double bond directly on the ring system, which is also referred to as exovinylene cyclocarbonate. There is no description of compounds having two or more exovinylene cyclocarbonate bonds.

U.S. Pat. No. 3,541,087 discloses compounds having two exovinylene cyclocarbonate groups that are connected to one another by a direct bond between the vinylene groups. WO 2015/010924 describes coating compositions comprising a compound having at least two cyclic exovinylene carbonate groups that are connected to one another via a siloxane group. WO 2013/144299 describes polymerizable alkylidene-1,3-dioxolan-2-ones, wherein the polymerization is effected by means of an ethylenically unsaturated group present on the alkylidene group as a substituent via a spacer. WO 2015/039807 describes coating compositions comprising, inter alia, an oligomeric or polymeric compound having at least two alkylidene-1,3-dioxolan-2-one groups. The dioxolanones are joined via the alkylidene groups.

WO 2015/164703 and WO 2015/164692 describe polycyclocarbonate compounds and polymers prepared therefrom. Executable disclosures are described only for compounds having two polycyclocarbonate groups.

Exovinylene cyclocarbonates can react at room temperature with amines to give urethanes and are hence a potential alternative to polyurethane formation by isocyanate/alcohol reactions. Unpublished European patent application having application Ser. No. 15/164,849.0 describes acrylate monomers comprising an exovinylene cyclocarbonate group. Multifunctional derivatives (copolymers) of these monomers are described in unpublished European patent application having application Ser. No. 15/172,703.9. However, these derivatives and monomers have to be synthesized over multiple stages with a distinct loss of yield.

It was an object of the invention to synthesize, from very simple precursors, a compound which comprises more than one exovinylene cyclocarbonate group and can serve as reactive unit for isocyanate-free two-component coating compositions which can cure even at room temperature if at all possible.

The invention provides a compound having two or more exovinylene cyclocarbonate units, where the exovinylene cyclocarbonate units are joined to one another via at least one organic, siloxane-free connecting group, where the connecting group is not present between the exovinylene groups and where connecting groups formed by polymerization of (meth)acrylic monomers are excluded. If the compound of the invention has two exovinylene cyclocarbonate units, the connecting group has at least one acetal group. If the compound of the invention has more than two exovinylene cyclocarbonate units, the connecting group preferably has at least one acetal group in the connecting group.

Preferably, the exovinylene cyclocarbonate units are 5-vinylidene-1,3-dioxolan-2-one units of the general formula (I)

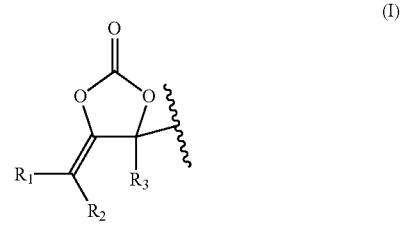

where the at least one organic, siloxane-free connecting group is between the 4 positions of the 5-vinylidene-1,3-dioxolan-2-one units and where R1 to R3 are independently hydrogen or an organic radical.

Preferably, R1 and R2 are independently a C1- to C10-alkyl group, a C1- to C6-alkyl group, a C1- to C3-alkyl group, a methyl group, or more preferably a hydrogen atom. Preferably, R3 is a C1- to C10-alkyl group, a C1- to C6-alkyl group, a C1- to C3-alkyl group, or a hydrogen atom, more preferably a methyl group. More preferably, R1, R2 and R3 are hydrogen or R1 and R2 are hydrogen and R3 is a methyl group.

Suitable compounds of the invention are, for example, those of the formula (II)

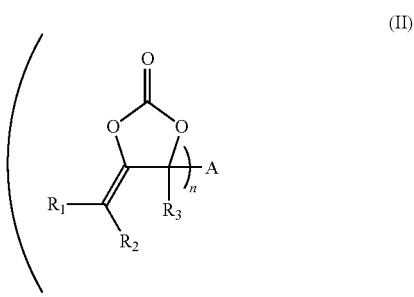

where R1 to R3 have the same definition as in formula (I); n is a number not less than 2, preferably 2 to 10 or 3 to 10; and A is a siloxane-free organic connecting group, excluding a connecting group formed by polymerization of (meth) acrylic monomers.

Preferably, -A is defined as —B-Q where B is a spacer group, for example a divalent hydrocarbyl group, especially an alkylene group having preferably 1 to 6 carbon atoms, e.g. butylene, propylene, ethylene or more preferably methylene; and where Q is an organic radical comprising at least one functional group selected from ether groups, polyether groups, ester groups, polyester groups, amide groups, polyamide groups, urethane groups, polyurethane groups, urea groups, polyurea groups, acetal groups and polyacetal groups, particular preference being given to ether groups, polyether groups, acetal groups and polyacetal groups.

Suitable examples include compounds of the formula (III)

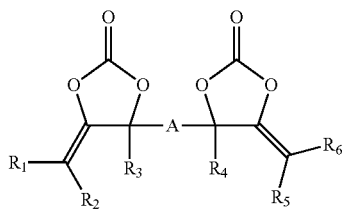

(III)

where R1 to R6 are each independently hydrogen or an organic radical. R1 to R3 preferably have the same definition as in formula (I). R5 and R6 preferably have the same definition as R1 and R2, and R4 preferably has the same definition as R3. A is a siloxane-free organic connecting group, excluding a connecting group formed by polymerization of (meth)acrylic monomers.

Preferably, -A- is defined as —B-Q-B— where B is a spacer group, for example a divalent hydrocarbyl group, especially an alkylene group having preferably 1 to 6 carbon atoms, e.g. butylene, propylene, ethylene or more preferably methylene; and where Q is an organic radical comprising at least one functional group selected from ether groups, polyether groups, ester groups, polyester groups, amide groups, polyamide groups, urethane groups, polyurethane groups, urea groups, polyurea groups, acetal groups and polyacetal groups, particular preference being given to ether groups, polyether groups, acetal groups and polyacetal groups.

Suitable examples also include compounds of the formula (IV)

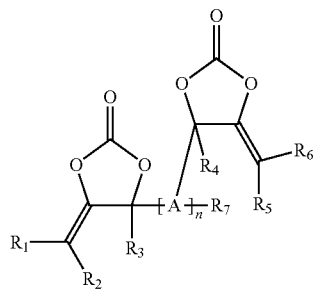

(IV)

or compounds of the formula (IVa)

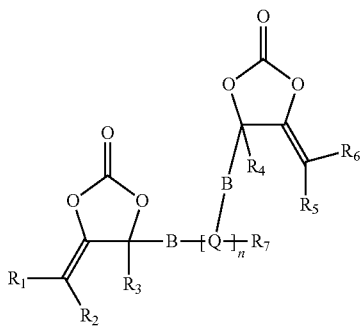

(IVa)

where R1 to R6, A, B and Q have the same definition as in formula (III) and R7 is hydrogen, an OH group or an organic radical, for example an alkyl, alkoxy or hydroxyalkyl group having 1 to 10 carbon atoms for example;
and where n is a number not less than 1, preferably 1 to 10 or 2 to 10.

Suitable examples also include compounds of the formula (V)

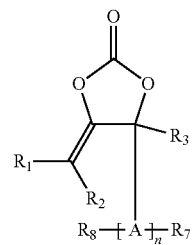

(V)

or compounds of the formula (Va)

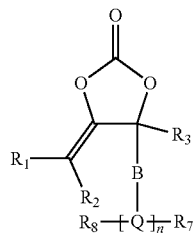

(Va)

where R1 to R3, A, B and Q have the same definition as in formula (III)
and R7 and R8 are independently hydrogen, an OH group or an organic radical, e.g. an alkyl, alkoxy or hydroxyalkyl group having 1 to 10 carbon atoms for example and where R7 and/or R8 may comprise an exovinylene group;
and n is a number not less than 1 if at least one of the R7 and R8 radicals comprises at least one exovinylene group and n is a number not less than 2, preferably 2 to 10 or 3 to 10, if neither of the R7 and R8 radicals comprises an exovinylene group.

In the compounds of the formulae (II) to (V), (IVa) and (Va), $R^1$, $R^2$, $R^5$ and $R^6$ are preferably independently a C1- to C10-alkyl group, a C1- to C6-alkyl group, a C1- to C3-alkyl group, or more preferably a hydrogen atom. $R^3$ and $R^4$ are preferably independently a C1- to C10-alkyl group, a C1- to C6-alkyl group, a C1- to C3-alkyl group or a hydrogen atom, more preferably a methyl group.

In the compounds of the formulae (II) to (V), (IVa) and (Va), $R^1$, $R^2$, $R^5$ and $R^6$ are more preferably each independently a hydrogen atom; $R^3$ and $R^4$ are independently methyl or a hydrogen atom; and $R^7$, $R^8$ and A are independently radicals of polyhydric alcohols having 2 to 12 carbon atoms that may also be interrupted by —O—, —S— or —$NR_2$— groups where R is H or C1- to C12-alkyl.

Preferably, the connecting group A in the compounds of the formulae (II) to (V) and the Q group in the compounds (II), (III), (IVa) and (Va) have at least one acetal group. Preferably, A is an organic radical having a total of not more than 24 carbon atoms, especially not more than 18 carbon atoms and more preferably not more than 14 carbon atoms. $R^1$ may, as well as oxygen, comprise further heteroatoms such as nitrogen or sulfur.

Preferably, -A- in compounds of the formula (III) is a structural element of the formula

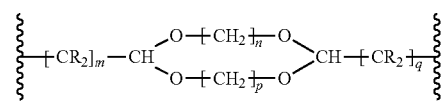

where R is a hydrocarbyl radical, e.g. a C1- to C10-alkyl group or preferably hydrogen and m, n, p and q are numbers from 1 to 10, where m and q are preferably 1 and n and p are preferably numbers from 4 to 10.

Preferred compounds are those of the formula (Vb)

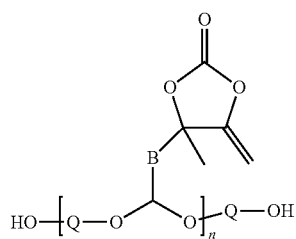

(Vb)

where B is an alkylene group having preferably 1 to 6 carbon atoms, e.g. butylene, propylene, ethylene or more preferably methylene;

Q is a group derived from a polyol, a polyol being an alcohol having at least two hydroxyl groups;

and n is a number not less than 2, preferably 2 to 10 or 3 to 10.

Suitable groups derived from a polyol are especially the groups derived from the alcoholic hardeners mentioned below, preferably selected from ethylene glycol, propane-1,3-diol, butane-1,4-diol, diethylene glycol, triethylene glycol, neopentyl glycol, pentane-1,5-diol, hexane-1,6-diol, octane-1,8-diol, 3-methylpentane-1,5-diol, 1,4-bis(hydroxymethyl)cyclohexane, 1,6-bis-(hydroxymethyl)cyclohexane, glycerol, diglycerol, polyethylene glycol, polypropylene glycol, poly-THF, pentaerythritol, dipentaerythritol, sugar alcohols such as sorbitol and mannitol.

Preferred compounds are also those of the formula (Vc)

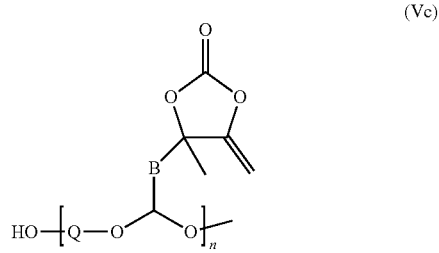

(Vc)

where B, Q and n have the same definition as in formula (Vb).

Preferred compounds are also those of the formula (IVb)

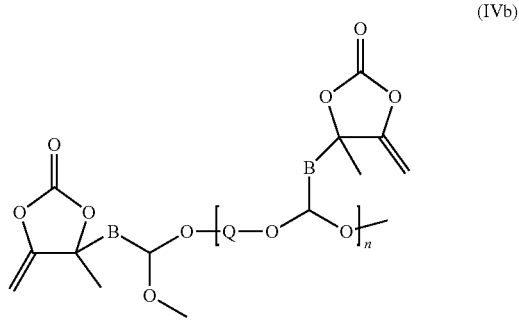

(IVb)

where B and Q have the same definition as in formula (Vb) and n is a number not less than 1, preferably 1 to 10 or 2 to 10.

Preferred compounds are also those of the formula (VI)

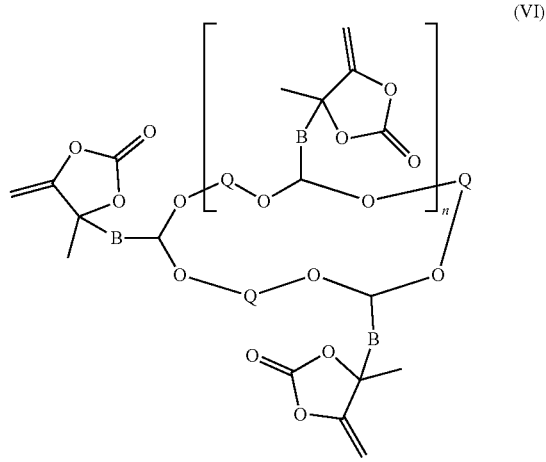

(VI)

where B and Q have the same definition as in formula (Vb) and n is a number not less than 0, preferably 0 to 10 or 1 to 5.

Examples of compounds of the invention include the following preferred compounds:

Compound of the formula (VIa):

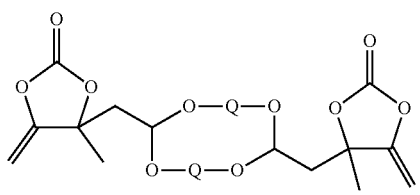

Compound of the formula (IVc):

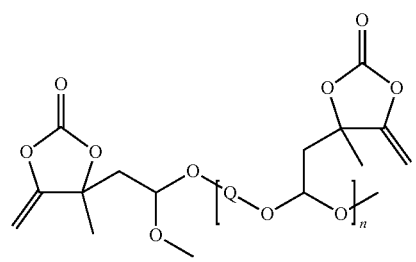

with n=1, 2 or 3.
Compound of the formula (Vd):

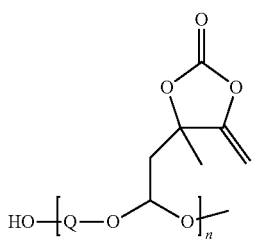

with n not less than 2, preferably 2 or 3.
Compound of the formula (Ve):

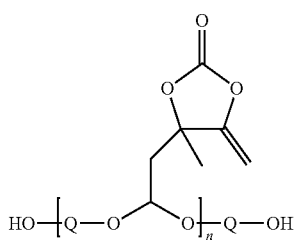

with n not less than 2, preferably 2 or 3.

Where —O-Q-O— in the formulae VIa, IVc, Vd and Ve is in each case the radical of a dihydric alcohol, preferably selected from ethylene glycol, propane-1,3-diol, butane-1,4-diol, diethylene glycol, triethylene glycol, neopentyl glycol, pentane-1,5-diol, hexane-1,6-diol, octane-1,8-diol, 3-methylpentane-1,5-diol, 1,4-bis(hydroxymethyl)cyclohexane, 1,6-bis(hydroxymethyl)-cyclohexane, glycerol, diglycerol, polyethylene glycol, polypropylene glycol, poly-THF, pentaerythritol, dipentaerythritol, sugar alcohols such as sorbitol and mannitol.

Compounds of the invention can be prepared, for example, by transacetalization of an exovinylene cyclocarbonate of the formula (VII)

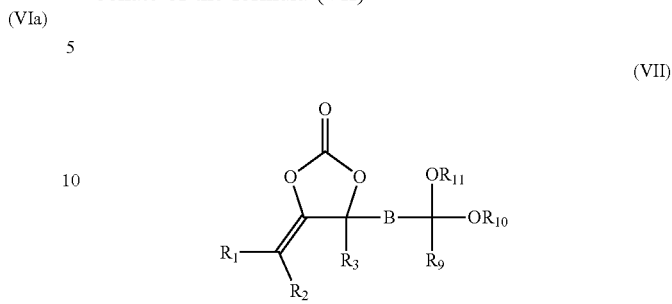

where R1 to R3 and R9 are independently hydrogen or an organic radical, R10 and R11 are independently an organic radical and B is an organic connecting group (spacer). R1 to R3 preferably have the same definition as in formula (I). R9 is preferably a C1- to C10-alkyl group, a C1- to C6-alkyl group, a C1- to C3-alkyl group, a methyl group or more preferably a hydrogen atom. R10 and R11 are preferably a C1- to C10-alkyl group, a C1- to C6-alkyl group or a C1- to C3-alkyl group, more preferably a methyl group. Preferably, in compounds of the formula (VII), $R^1$ and $R^2$ are each a hydrogen atom; $R^3$ and $R^9$ are independently methyl or a hydrogen atom; $R^{10}$ and $R^{11}$ are independently hydrocarbyl groups, especially $C_1$- to $C_{10}$-alkyl groups or alkyl groups having 1 to 4 carbon atoms, more preferably methyl groups. B is preferably an alkylene group having 1 to 4 carbon atoms, especially methylene.

Particular preference is given to a compound of the formula (VIIa):

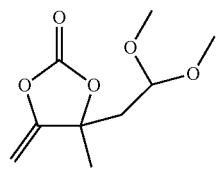

Exovinylene cyclocarbonates suitable for a transacetalization may be prepared, for example, by a process in which
in a first stage a compound having a terminal triple bond is reacted with an alkanone or alkanal comprising an acetal group, with addition of the triple bond onto the carbonyl group of the alkanone or alkanal to form a hydroxyl compound,
in a second stage the ring is closed with carbon dioxide to give the carbonate group.

Stage 1

The reaction in the first stage is an addition, known per se, of triple bonds onto a carbonyl group. Suitable compounds having a terminal triple bond are especially compounds of the formula (VIII)

Y—CH=CH where Y is a hydrogen atom, a hydrocarbyl group having 1 to 10 carbon atoms, e.g. an alkyl or aryl group or a protecting group having a maximum of 10 carbon atoms. If Y is not a protecting group, the substituents of the Y-substituted carbon atom determine the later R1, R2, R5 and R6 radicals in the formulae (I) to (V). Proceeding from formula (VIII), therefore, one of the R1 or R2 radicals or one of the R5 or R6 radicals in formulae (I) to (V) is a hydrogen atom and the respective other is Y. The preferred definitions of Y therefore correspond to the above preferred definitions of R1, R2, R5 and R6.

However, Y may also be a protecting group. Protecting groups are detached again during or on completion of synthesis, such that, in this case, the later R1 and R2 or R5 and R6 radicals in formulae (I) to (V) and (VII) are each a hydrogen atom. An example of a suitable protecting group is the trimethylsilyl group (TMS for short).

There are various known methods for performance of the addition reaction. Preferably, the starting compounds are converted in the presence of a strong base. Preferred strong bases are metal alkoxides. These are preferably metal salts of aliphatic alcohols, especially metal salts of C1 to C8 alcohols, preferably C2 to C6 alcohols, such as ethanol, n-propanol, isopropanol, n-butanol or tert-butanol. The metal cations of the metal alkoxides are preferably alkali metal cations, for example the cations of sodium or potassium. Examples of preferred metal alkoxides include potassium tert-butoxide, sodium tert-butoxide, potassium isopropoxide and sodium isopropoxide.

The reaction is preferably conducted in the presence of a solvent. Preferred solvents are inert solvents; these do not comprise any reactive groups which react with the starting compounds. Particular preference is given to inert polar aprotic solvents. Examples of these include cyclic ether compounds, especially THF. The reaction is generally exothermic; therefore, cooling is preferably effected in the course of reaction. The temperature of the reaction mixture is preferably not more than 50° C., especially not more than 25° C.; it is preferably between 0 and 25° C.

For workup of the resultant product mixture, it is possible to add water, optionally acid and optionally a nonpolar organic solvent. If the product of value from the 1st stage already forms a separate organic phase, it is possible to dispense with the organic solvent. Two phases form, of which it is the organic phase that comprises the product of the 1st stage (addition products). The organic phase can be dried for removal of water. Solvent can be removed easily by distillation. The product can be obtained in pure form by vacuum distillation. Alternatively, the workup can also be effected by customary methods of crystallization or extraction, especially when the product of the 1st stage has a very high boiling point.

The alkanones or alkanals used comprise an acetal group. Preferred alkanones or alkanals having an acetal group are those of the formula IX

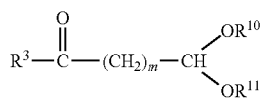

in which $R^3$ is a hydrogen atom or a C1- to C10-alkyl group, m is 0 or an integer from 1 to 10. m is 0 or an integer from 1 to 10. Preferably, m is an integer from 1 to 10, especially an integer from 1 to 6, and m is most preferably 1. The group

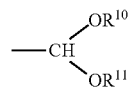

is the acetal group where $R^{10}$ and $R^{11}$ are hydrocarbyl groups, especially $C_1$- to $C_{10}$-alkyl groups or alkyl groups having 1 to 4 carbon atoms, more preferably methyl groups. $R^3$ corresponds to the $R^3$ or $R^4$ in the formulae I to V and VII and has the corresponding definitions and preferred definitions; in a preferred embodiment, $R^3$ is a methyl group.

There are various known methods for performance of the addition reaction. Preferably, the starting compounds are converted in the presence of a strong base. Preferred strong bases are metal alkoxides. These are preferably metal salts of aliphatic alcohols, especially metal salts of C1 to C8 alcohols, preferably C2 to C6 alcohols, such as ethanol, n-propanol, isopropanol, n-butanol or tert-butanol. The metal cations of the metal alkoxides are preferably alkali metal cations, for example the cations of sodium or potassium. Examples of preferred metal alkoxides include potassium tert-butoxide, sodium tert-butoxide, potassium isopropoxide and sodium isopropoxide.

The reaction is preferably conducted in the presence of a solvent. Preferred solvents are inert solvents; these do not comprise any reactive groups which react with the starting compounds. Particular preference is given to inert polar aprotic solvents. Examples of these include cyclic ether compounds, especially THF. The reaction is generally exothermic; therefore, cooling is preferably effected in the course of reaction. The temperature of the reaction mixture is preferably not more than 50° C., especially not more than 25° C.; it is preferably between 0 and 25° C.

For workup of the resultant product mixture, it is possible to add water, optionally acid and optionally a nonpolar organic solvent. If the product of value from the 1st stage already forms a separate organic phase, it is possible to dispense with the organic solvent. Two phases form, of which it is the organic phase that comprises the product of the 1st stage (addition products). The organic phase can be dried for removal of water. Solvent can be removed easily by distillation. The product can be obtained in pure form by vacuum distillation. Alternatively, the workup can also be effected by customary methods of crystallization or extraction, especially when the product of the 1st stage has a very high boiling point.

Stage 2

In stage 2, the ring is closed with carbon dioxide to form the cyclic carbonate group. The product of the second stage is a compound having a cyclic carbonate group and an acetal group. For this purpose, carbon dioxide, preferably in gaseous form or in the supercritical state, is contacted with the starting compound under pressure. The reaction is therefore preferably conducted in an autoclave. Carbon dioxide can also be used in a mixture with inert gas.

The reaction is preferably effected in the presence of catalysts. It is preferably effected in the presence of a base as catalyst or more preferably in the presence of a catalyst system composed of a base and a metal salt. Preferred bases are compounds having at least one tertiary amino group, for example having one to three tertiary amino groups. Bases of this kind are known. They typically have a molar mass below 500 g/mol, especially below 300 g/mol. They are especially aliphatic or cycloaliphatic compounds.

Examples of bases include
TMTACN (N,N',N"-trimethyl-1,4,7-triazacyclononane)
PMDETA (pentamethyldiethylenetriamine)
TMEDA (tetramethylethylenediamine)
DBU (1,8-diazabicyclo[5.4.0]undec-7-ene) or
DBN (1,5-diazabicyclo[4.3.0]non-5-ene).

The metal salt preferably comprises salts having mono- to trivalent cations, especially cations of Cu, Ag or Au. The anion of the metal salts is preferably a carboxylate, especially a C1- to C6-carboxylate. Preferred metal salts include silver acetate and copper acetate.

Phosphines are also useful as catalysts. These are especially trialkyl- or triarylphosphines. These can be used alone or likewise in combination with a metal salt.

The reaction is conducted preferably at a pressure of 1 to 100 bar, especially 5 to 70 bar. The temperature of the reaction mixture is preferably 10 to 100° C., especially 10 to 80° C. The reaction can be monitored, for example, by gas chromatography.

After cooling and decompression, the resultant product can be worked up. It is possible to add an organic solvent, preferably an inert, hydrophobic organic solvent such as dichloromethane or toluene, and aqueous acid, for example HCl, such that two phases form. The organic phase comprises the desired product. Water can be removed from the organic phase by drying. Solvent can be removed by distillation. The product can be purified by distillation. A gentle and therefore preferred distillation is, for example, distillation in a thin-film evaporator. Especially suitable for this purpose are thin-film evaporators having a wiper system. An alternative option in the case of high boiling points of the product of the second stage is a workup and purification by crystallization or extraction.

Transacetalization:

The transacetalization, for example of reaction products from stage 2, can be conducted with alcohols under catalysis with Lewis acids or protic acids, the latter giving better yields. Acidic catalysts are, for example, acidic inorganic, organometallic or organic catalysts or mixtures of multiple acidic inorganic, organometallic or organic catalysts. Acidic inorganic catalysts include, for example, sulfuric acid, sulfates and hydrogensulfates, such as sodium hydrogensulfate, phosphoric acid, phosphonic acid, hypophosphorous acid, aluminum sulfate hydrate, alum, acidic silica gel (pH≤6, especially ≤5) and acidic alumina. In addition, for example, aluminum compounds of the general formula $Al(OR^1)_3$ and titanates of the general formula $Ti(OR^1)_4$ are usable as acidic inorganic catalysts, where the $R^1$ radicals may each be the same or different and are independently selected from $C_1$-$C_{20}$-alkyl radicals, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, 2-ethylhexyl, n-nonyl, n-decyl, n-dodecyl, n-hexadecyl or n-octadecyl; $C_3$-$C_{12}$-cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl. Preferred acidic organometallic catalysts are, for example, selected from dialkyltin oxides $R^1_2SnO$ or dialkyltin esters $R^1_2Sn(OR^2)_2$ where $R^1$ is as defined above and may be the same or different. $R^2$ may have the same definitions as $R^1$ and may additionally be $C_6$-$C_{12}$-aryl, for example phenyl, o-, m- or p-tolyl, xylyl or naphthyl. $R^2$ may be the same or different in each case. Examples of organotin catalysts are tin(II) n-octanoate, tin(II) 2-ethylhexanoate, tin(II) laurate, dibutyltin oxide, diphenyltin oxide, dibutyltin dichloride, dibutyltin diacetate, dibutyltin dilaurate, dibutyltin dimaleate or dioctyltin diacetate. Particularly preferred representatives of acidic organometallic catalysts are dibutyltin oxide, diphenyltin oxide and dibutyltin dilaurate.

Preferred acidic organic catalysts are acidic organic compounds having, for example, phosphate groups, sulfonic acid groups, sulfate groups or phosphonic acid groups. It is also possible to use acidic ion exchangers as acidic organic catalysts, for example sulfo-containing polystyrene resins that have been crosslinked with about 2 mol % of divinylbenzene. Particular preference is given to sulfonic acids, for example p-toluenesulfonic acid or methanesulfonic acid; and trifluoroacetic acid. The catalysts may be homogeneous or else heterogeneous or supported. Stronger acids tend to discolor the reaction products; weaker acids require higher temperatures.

The alcohols may be primary, secondary or tertiary, preference being given to primary alcohols. Diols are particularly preferred since they lead to linear oligomers. If polyols having three or more hydroxyl groups are used, the molecular weight and branching can also be controlled by additional use of monools. Mixtures of alcohols are likewise possible. The molecular weights of the diols are preferably from 62 to 5000 g/mol, more preferably from 90 to 2000 g/mol (in the case of polymers: number-average molecular weight Mn from end group analysis).

The ratio of OR groups of the acetal groups to OH groups may be 4:1 to 1:4, preferably 2:1 to 1:2, most preferably 1.5:1 to 1:1.5.

The reaction can be conducted in various solvents, preference being given to polar solvents, for example acetonitrile. Reaction temperatures are between room temperature (20° C.) and 100° C., preferably <80° C., more preferably <60° C. The reaction is more preferably conducted under reduced pressure for effective removal of the methanol from the equilibrium. For this purpose, it is particularly preferable when the reaction is conducted in a solvent-free manner for prolonged periods. For instance, the reaction mixture can first be made up in solution for better homogenization and the solvent can then be removed under reduced pressure. It can also be recovered and reused.

The reaction products of the invention (oligomeric exovinylene cyclocarbonate acetals) can be worked up by simply washing out the catalyst. If the catalyst is supported, it merely has to be filtered. Higher purities result from extractive shaking with water, buffers or fairly weak bases and drying with desiccants. Precipitations in water and nonsolvents are also possible, although care should be taken that the acetal groups are not hydrolyzed.

The exovinylene cyclocarbonates of the invention have weight-average molecular weights Mw preferably between 500 and 50 000 g/mol, more preferably between 1000 and 10 000 g/mol, measured via gel permeation chromatography (GPC in THF; polystyrene standard). The viscosity is preferably 0.5 to 5000 Pa s (measured as zero-shear viscosity). The zero-shear viscosity is the limiting value of the viscosity function at infinitely low shear rates. It is measured with an Anton Paar MCR 100 rheometer (US 200 evaluation software) in plate/plate geometry. The samples are analyzed in oscillatory shear at a small shear amplitude of 10% and at a temperature of 23° C., angular frequency ramp: log 100-0.1 1/s, measurement gap 0.5 mm, evaluation according to Carreau-Gahleitner I, die diameter 25 mm.

The exovinylene cyclocarbonates of the invention can be chain-extended with isocyanates, acid chlorides and/or acid anhydrides without destroying the exovinylene carbonate ring. They can also be reacted by ring-opening with polyamines to give polyurethanes. They can also be reacted with further polyols by ring-opening under highly basic catalysis to give polycarbonates. The invention also provides a process for preparing a compound having two or more exovinylene cyclocarbonate units, wherein a compound having an exovinylene cyclocarbonate unit and at least one acetal group is reacted in a transacetalization reaction with at least one compound selected from the group consisting of diols and polyols. The reaction is preferably conducted with catalysis by Lewis acids or by protic acids.

The invention also provides the reaction products of the process.

The invention also provides for the use of the compounds of the invention as a constituent of coating compositions, varnishes, paints, inks, building materials, elastomers or foams, or for binding of fibers and/or particles.

Blends of the compounds of the invention with a polyfunctional hardener component can be used as two-component binders. The invention therefore also provides for uses of two-component binders comprising at least one compound of the invention in a first component and, in a second component, at least one polyfunctional hardener having at least two functional groups selected from the group consisting of primary amino groups, secondary amino groups, hydroxyl groups, phosphine groups, phosphonate groups and mercaptan groups. The two-component binder preferably comprises at least one catalyst for the catalysis of the reaction of the exovinylene cyclocarbonate groups with the functional groups of the hardener. The two-component binder may be applied as a solution in an organic solvent or as a solvent- and water-free neat system.

Preferably, the functional groups of the hardener are selected from aliphatic hydroxyl groups, aliphatic primary amino groups, aliphatic secondary amino groups, aliphatic phosphine groups, aliphatic phosphonate groups and aliphatic mercaptan groups.

Two-component binders (2K binders) are understood to mean a binder comprising at least two polyfunctional binder constituents which react with one another to form bonds and in doing so form a polymeric network. Due to the alkylidene-1,3-dioxolan-2-one groups present therein, the polymers of the invention can react with numerous nucleophilic groups to form bonds. Examples of such nucleophilic groups are particularly aliphatic hydroxyl groups, aliphatic primary and secondary amino groups, phosphine groups, especially aliphatic phosphine groups, phosphonate groups, especially aliphatic phosphonate groups, and analogous phosphorus compounds, and also mercaptan groups, especially aliphatic mercaptan groups.

Accordingly, two-component binder compositions comprise, as well as at least one polymer of the invention, preferably additionally at least one compound having at least 2 functional groups F, for example 2, 3, 4, 5, 6, 7, 8, 9 or 10 functional groups F, which are selected from aliphatic hydroxyl groups, aliphatic primary or secondary amino groups, aliphatic phosphine groups, aliphatic phosphonate groups and similar groups, and aliphatic mercaptan groups. These compounds are also referred to hereinafter as hardeners. Preferred functional groups F are aliphatic hydroxyl groups and aliphatic primary and secondary amino groups. Preferably, the amount of hardener is selected such that the molar ratio of functional alkylidene-1,3-dioxolan-2-one groups of the formula I to the functional groups F in the hardener is in the range from 1:10 to 10:1, particularly in the range from 5:1 to 1:5 and especially in the range from 1:2 to 2:1.

The hardener may be a low molecular weight substance, which means that the molecular weight thereof is below 500 g/mol, or an oligomeric or polymeric substance having a number-average molecular weight above 500 g/mol.

The hardeners preferred in accordance with the invention include aminic hardeners, i.e. hardeners which have at least two primary or secondary amino groups, and alcoholic hardeners, i.e. compounds which have at least two hydroxyl groups.

The aminic hardeners, also amine hardeners hereinafter, include, for example, aliphatic and cycloaliphatic polyamines, aromatic and araliphatic polyamines and polymeric amines, for example amino resins and polyamidoamines. Amine hardeners crosslink polymers having 1,3-dioxolan-2-one groups, also called carbonate polymers hereinafter, by reaction of the primary or secondary amino functions of the polyamines with the 1,3-dioxolan-2-one groups of the carbonate polymers to form urethane functions. Preferred polyamine hardeners have an average of at least two primary or secondary amino groups per molecule, for example two, three or four primary or secondary amino groups per molecule. They may also additionally comprise one or more tertiary amino groups. Suitable polyamines are, for example, aliphatic polyamines such as ethylenediamine, 1,2- and 1,3-propanediamine, neopentanediamine, hexamethylenediamine, octamethylenediamine, 1,10-diaminodecane, 1,12-diaminododecane, diethylenetriamine, triethylenetetramine, tetraethylenepentamine, 2,2-dimethylpropylenediamine, trimethylhexamethylenediamine, 1-(3-aminopropyl)-3-aminopropane, 1,3-bis(3-aminopropyl)propane, 4-ethyl-4-methylamino-1-octylamine, and the like;

cycloaliphatic diamines, such as 1,2-diaminocyclohexane, 1,2-, 1,3-, 1,4-bis(amino-methyl)cyclohexane, 1-methyl-2,4-diaminocyclohexane, N-cyclohexylpropylene-1,3-diamine, 4-(2-aminopropan-2-yl)-1-methylcyclohexane-1-amine, isophoronediamine, 4,4'-diaminodicyclohexylmethane (Dicykan), 3,3'-dimethyl-4,4'-diaminodicyclohexylmethane, 3,3',5,5'-tetramethyl-4,4'-diaminodicyclohexylmethane, 4,8-diaminotricyclo[5.2.1.0]decane, norbornanediamine, menthanediamine, menthenediamine, and the like;

aromatic diamines, such as tolylenediamine, xylylenediamine, especially meta-xylylenediamine (MXDA), bis(4-aminophenyl)methane (MDA or methylenedianiline), bis(4-aminophenyl) sulfone (also known as DADS, DDS or dapsone), and the like;

cyclic polyamines, such as piperazine, N-aminoethylpiperazine, and the like;

polyetheramines, especially difunctional and trifunctional primary polyetheramines based on polypropylene glycol, polyethylene glycol, polybutylene oxide, poly(1,4-butanediol), polytetrahydrofuran (polyTHF) or polypentylene oxide, for example 4,7,10-trioxatridecane-1,3-diamine, 4,7,10-trioxatridecane-1,13-diamine, 1,8-diamino-3,6-dioxaoctane (XTJ-504 from Huntsman), 1,10-diamino-4,7-dioxadecane (XTJ-590 from Huntsman), 1,12-diamino-4,9-dioxadodecane (from BASF SE), 1,3-diamino-4,7,10-trioxatridecane (from BASF SE), primary polyetheramines based on polypropylene glycol having an average molar mass of 230, for example Polyetheramine D 230 (from BASF SE) or Jeffamine® D 230 (from Huntsman), difunctional, primary polyetheramines based on polypropylene glycol having an average molar mass of 400, e.g. Polyetheramine D 400 (from BASF SE) or Jeffamine® XTJ 582 (from Huntsman), difunctional, primary polyetheramines based on polypropylene glycol having an average molar mass of 2000, for example Polyetheramine D 2000 (from BASF SE), Jeffamine® D2000 or Jeffamine® XTJ 578 (each from Huntsman), difunctional, primary polyetheramines based on propylene oxide having an average molar mass of 4000, for example Polyetheramine D 4000 (from BASF SE), trifunctional, primary polyetheramines prepared by reacting propylene oxide with trimethylolpropane followed by an amination of the terminal OH groups, having an average molar mass of 403, for example Polyetheramine T 403 (from BASF SE) or Jeffamine® T 403 (from Huntsman), trifunctional, primary polyetheramine prepared by reacting propylene oxide with glycerol, followed by an amination of the terminal OH groups, having an average molar mass of 5000, for example Polyetheramine T 5000 (from BASF SE) or Jeffamine® T 5000 (from Huntsman), aliphatic polyetheramines formed from a propylene oxide-grafted polyethylene glycol and having an average molar mass of 600, for example Jeffamine® ED-600 or Jeffamine® XTJ 501 (each from Huntsman), aliphatic polyetheramines formed from a propylene oxide-grafted polyethylene glycol and having an average molar mass of 900, for example Jeffamine® ED-900 (from Huntsman), aliphatic polyetheramines formed from a propylene oxide-grafted polyethylene glycol and having an average molar mass of 2000, for example Jeffamine® ED-2003 (from Huntsman), difunctional, primary polyetheramine prepared by amination of a propylene oxide-grafted diethylene glycol, having an average molar mass of 220, for example Jeffamine® HK-511 (from Huntsman), aliphatic polyetheramines based on a copolymer of poly(tetramethylene ether glycol) and polypropylene glycol having an average molar mass of 1000, for example Jeffamine® XTJ-542 (from Huntsman), aliphatic polyetheramines based on a copolymer of poly(tetramethylene ether glycol) and polypropylene glycol having an average molar mass of 1900, for example Jeffamine® XTJ-548 (from Huntsman), aliphatic polyetheramines based on a copolymer of poly (tetramethylene ether glycol) and polypropylene glycol having an average molar mass of 1400, for example Jeffamine® XTJ-559 (from Huntsman), polyethertriamines based on a butylene oxide-grafted, at least trihydric alcohol having an average molar mass of 400, for example Jeffamine® XTJ-566 (from Huntsman), aliphatic polyetheramines prepared by amination of butylene oxide-grafted alcohols having an average molar mass of 219, for example Jeffamine® XTJ-568 (from Huntsman), polyetheramines based on pentaerythritol and propylene oxide having an average molar mass of 600, for example Jeffamine® XTJ-616 (from Huntsman), polyetheramines based on triethylene glycol having an average molar mass of 148, for example Jeffamine® EDR-148 (from Huntsman), difunctional, primary polyetheramines prepared by amination of a propylene oxide-grafted ethylene glycol, having an average molar mass of 176, for example Jeffamine® EDR-176 (from Huntsman), and also polyetheramines prepared by amination of polytetrahydrofuran (polyTHF) having an average molar mass of 250, for example PolyTHF-amine 350 (BASF SE), and mixtures of these amines;

polyamidoamines (amidopolyamines), which are obtainable by reaction of dimeric fatty acids (for example dimeric linoleic acid) with polyamines of low molecular weight, such as diethylenetriamine, 1-(3-aminopropyl)-3-aminopropane or triethylenetetramine, or other diamines, such as the aforementioned aliphatic or cycloaliphatic diamines;

adducts obtainable by reaction of amines, especially diamines, with a deficiency of epoxy resin or reactive diluent, preference being given to using those adducts in which about 5% to 20% of the epoxy groups have been reacted with amines, especially diamines;

phenalkamines as known from epoxide chemistry;

Mannich bases which are prepared, for example, by condensation of polyamines, preferably diethylenetriamine, triethylenetetramine, isophoronediamine, 2,2,4- or 2,4,4-trimethylhexamethylenediamine, 1,3- and 1,4-bis(aminomethyl)cyclohexane, with aldehydes, preferably formaldehyde, and mono- or polyhydric phenols having at least one aldehyde-reactive core site, for example the various cresols and xylenols, p-tert-butylphenol, resorcinol, 4,4'-dihydroxydiphenylmethane, 4,4'-dihydroxydiphenyl-2,2-propane, but preferably phenol;

and mixtures of the aforementioned amine hardeners, especially mixtures of difunctional amines from the group of the aliphatic, cycloaliphatic and aromatic amines with the aforementioned polyetheramines.

Preferred aminic hardeners are aliphatic polyamines, especially 2,2-dimethylpropylenediamine, aromatic diamines, especially m-xylylenediamine (MXDA) and cycloaliphatic diamines, especially isophoronediamine, N-cyclohexylpropylene-1,3-diamine and 4,4'-diaminodicyclohexylmethane (Dicykan). Preference is also given to difunctional or trifunctional primary polyetheramines based on polypropylene glycol, for example Jeffamine® D 230 or Jeffamine® T 403. Particular preference is given to polyamines in which there is high mobility and low steric hindrance around the amino group, for example 4,9-dioxadodecane-1,12-diamine, 4,7,10-trioxatridecane-1,13-diamine, PolyTHF Amine 350 (BASF SE).

Preference is also given to mixtures of the amines specified as preferred, for example mixtures comprising 2,2-dimethylpropyleneamine and isophoronamine.

The alcoholic hardeners include particularly aliphatic and cycloaliphatic alcohols of low molecular weight and higher molecular weight. Alcoholic hardeners crosslink to give carbonate polymers by reaction of the primary or secondary alcohol functions with the 1,3-dioxolan-2-one groups to form diesters of carbonic acid. Preferred alcoholic hardeners have an average of at least two primary or secondary hydroxyl groups per molecule, for example two, three or four primary or secondary hydroxyl groups per molecule. Suitable alcoholic hardeners of low molecular weight are, for example, butane-1,4-diol, ethylene glycol, diethylene glycol, triethylene glycol, neopentyl glycol, propane-1,3-diol, pentane-1,5-diol, hexane-1,6-diol, glycerol, diglycerol, pentaerythritol, dipentaerythritol, sugar alcohols such as sorbitol and mannitol.

Suitable alcoholic hardeners are also higher molecular weight polymeric polyols, for example polyester polyols, polycarbonate polyols, polyether polyols, polyacrylate polyols and polyvinyl alcohols. Suitable polymeric polyol hardeners preferably have a mean OH functionality of at least 1.5 mol and especially at least 1.8, for example in the range from 1.5 to 10 and especially in the range from 1.8 to 4. The mean OH functionality is understood to mean the mean number of OH groups per polymer chain. Typical polymeric polyol components preferably have a number-average molecular weight of about 250 to 50 000 g/mol, preferably of about 500 to 10 000 g/mol. Preferably, at least 50 mol % of the hydroxyl groups present in the polymeric polyol component are primary hydroxyl groups.

Preferably, polyester polyols are linear or branched polymeric compounds having ester groups in the polymer backbone and having free hydroxyl groups at the ends of the polymer chain. Preferably, these are polyesters which are obtained by polycondensation of dihydric alcohols with dibasic carboxylic acids, optionally in the presence of higher polyhydric alcohols (e.g. tri-, tetra-, penta- or hexahydric alcohols) and/or higher polybasic polycarboxylic acids. Rather than the free di- or polycarboxylic acids, it is also possible to use the corresponding di- or polycarboxylic anhydrides or corresponding di- or polycarboxylic esters of lower alcohols or mixtures thereof for preparation of the polyester polyols. The di- or polycarboxylic acids may be aliphatic, cycloaliphatic, araliphatic, aromatic or heterocyclic, preferably have 2 to 50 and especially 4 to 20 carbon atoms and may optionally be substituted, for example by halogen atoms, and/or be unsaturated. Examples thereof include: suberic acid, azelaic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, alkenylsuccinic acid, fumaric acid and dimeric fatty acids. Useful diols for the preparation of the polyester polyols include especially aliphatic and cycloaliphatic diols having preferably 2 to 40 and especially 2 to 20 carbon atoms, for example ethylene glycol, propane-1,2-diol, propane-1,3-diol, butane-1,3-diol, butane-1,4-diol, butene-1,4-diol, butyne-1,4-diol, pentane-1,5-diol, neopentyl glycol, bis(hydroxymethyl)cyclohexanes such as 1,4-bis(hydroxymethyl)cyclohexane, 2-methylpropane-1,3-diol, methylpentanediols, and also diethylene glycol, triethylene glycol, tetraethylene glycol, polyethylene glycol, dipropylene glycol, polypropylene glycol, dibutylene glycol and polybutylene glycols. Preference is given to alcohols of the general formula HO—$(CH_2)_x$—OH, where x is a number from 2 to 20, preferably an even number from 2 to 12. Examples thereof are ethylene glycol, butane-1,4-diol, hexane-1,6-diol, octane-1,8-diol and dodecane-1,12-diol. Additionally preferred are neopentyl glycol and pentane-1,5-diol.

Suitable alcoholic hardeners are also lactone-based polyester polyols, these being homo- or copolymers of lactones, preferably terminal hydroxyl-containing addition products of lactones onto suitable difunctional starter molecules. Useful lactones are preferably those which derive from compounds of the general formula HO—$(CH_2)_z$—COOH where z is a number from 1 to 20 and one hydrogen atom of one methylene unit may also be substituted by a $C_1$-$C_4$-alkyl radical. Examples are ε-caprolactone, β-propiolactone, γ-butyrolactone and/or methyl-ε-caprolactone and mixtures thereof. Suitable starter molecules are, for example, the low molecular weight dihydric alcohols mentioned above as a formation component for the polyester polyols. The corresponding polymers of ε-caprolactone are particularly preferred. It is also possible to use lower polyester diols or polyether diols as starters for preparation of the lactone polymers. Rather than the polymers of lactones, it is also possible to use the corresponding chemically equivalent polycondensates of the hydroxycarboxylic acids corresponding to the lactones.

Examples of suitable polyester polyols are, for example, the polyester polyols known from Ullmanns Enzyklopadie der Technischen Chemie [Ullmann's Encyclopedia of Industrial Chemistry], 4th Edition, Volume 19, pages 62 to 65.

In addition, polycarbonate polyols are also useful, as obtainable, for example, by reaction of phosgene with an excess of the low molecular weight alcohols mentioned as formation components for the polyester polyols.

The polyether polyols are especially polyether polyols preparable by polymerization of ethylene oxide, propylene oxide, butylene oxide, tetrahydrofuran, styrene oxide or epichlorohydrin with themselves, for example in the presence of $BF_3$ or by addition of these compounds, optionally in a mixture or in succession, onto bi- or polyfunctional starter components having reactive hydrogen atoms, such as polyols or polyfunctional amines, for example water, ethylene glycol, propane-1,2-diol, propane-1,3-diol, 1,1-bis(4-hydroxyphenyl)propane, trimethylolpropane, glycerol, sorbitol, ethanolamine or ethylenediamine. Also useful are sucrose polyethers (see DE 1176358 and DE 1064938), and formitol- or formose-started polyethers (see DE 2639083 and DE 2737951).

Likewise suitable are polyhydroxy olefins, preferably those having 2 terminal hydroxyl groups, e.g. α,ω-dihydroxypolybutadiene.

Likewise suitable are polyhydroxypolyacrylates, where the hydroxyl groups may be arranged laterally or terminally. Examples thereof are α,ω-dihydroxypoly(meth)acrylic esters obtainable by homo- or copolymerization of alkyl esters of acrylic acid and/or of methacrylic acid in the presence of regulators comprising OH groups, such as mercaptoethanol or mercaptopropanol, and subsequent transesterification with a low molecular weight polyol, for example an alkylene glycol such as butanediol. Such polymers are known, for example, from EP-A 622 378. Examples thereof are additionally polymers obtainable by copolymerization of alkyl esters of acrylic acid and/or of methacrylic acid with hydroxyalkyl esters of ethylenically unsaturated carboxylic acid such as hydroxyethyl acrylate, hydroxypropyl acrylate, hydroxybutyl acrylate, hydroxyethyl methacrylate, hydroxypropyl methacrylate or hydroxybutyl methacrylate.

Also suitable are polyvinyl alcohols, which can preferably be obtained by full or partial hydrolysis of polyvinyl esters, especially polyvinyl acetate. If the polyvinyl esters, preferably polyvinyl acetate, are in partly hydrolyzed form, preferably not more than 50% to 95% of the ester groups are in hydrolyzed form as hydroxyl groups. If the polyvinyl esters, preferably polyvinyl acetate, are in fully hydrolyzed form, generally more than 95% up to 100% of the ester groups are in hydrolyzed form as hydroxyl groups.

Alcoholic hardeners preferred among the higher molecular weight polymeric polyols are especially polyacrylate polyols, these being obtainable, for example, under the Joncryl® brand name from BASF SE, e.g. Joncryl® 945.

Suitable hardeners are also amino acids, for example lysine, arginine, glutamine and asparagine, and the stereoisomers thereof and mixtures thereof.

It will be appreciated that it is also possible to use mixtures of different hardeners, for example mixtures of one or more aminic hardeners with one or more alcoholic hardeners, mixtures of one or more aminic hardeners with one or more amino acids, or mixtures of one or more alcoholic hardeners with one or more amino acids.

In the binder compositions of the invention, the total amount of hardeners is preferably 0.1% by weight to 50% by weight, frequently 0.5% to 40% by weight and especially 1% to 30% by weight, based on the total amount of exovinylene cyclocarbonate compounds plus hardeners used.

The binder composition can be hardened thermally by heating the mixture of polymer of the invention and hardener to a temperature above the mixing temperature. The hardening can also be effected at lower temperatures. Typically, the binder compositions of the invention are hardened at temperatures in the range from −10 to 150° C., preferably in the range from 0 to 100° C. and especially in the range from 10 to 70° C. Hardening is particularly advantageously effected at temperatures of 20-30° C. The temperature which is suitable depends on the respective hardeners and the desired hardening rate, and can be determined in the individual case by the person skilled in the art, for example by simple preliminary tests. In the lower temperature range (5 to about 35° C.), which of course corresponds to the usually prevailing ambient temperature, it is of course sufficient to mix polymer of the invention and hardener. Alternatively, the hardening is preferably microwave-induced.

The two-component binder compositions may also comprise one or more suitable catalysts for the hardening, which are guided in a known manner by the nature of the reactive functional groups F. The catalysts are, if desired, used in proportions of 0.01% by weight to about 10% by weight, based on the total weight of the polymers of the invention having functional alkylidene-1,3-dioxolan-2-one groups of the formula I and of the hardener. In one configuration, no catalysts are required, particularly in the case of hardeners which have amino groups as functional groups, which means that the content of catalysts in the composition in that case is less than 0.01% by weight. Catalysts are used with preference when the hardener has reactive groups F other than amino groups, especially when the hardener has hydroxyl groups.

Catalysts used with preference are basic catalysts, more preferably organic amines and organic phosphines. Among the organic amines, preference is given to amidine bases, for example 1,8-diazabicyclo[5.4.0]undec-7-ene (DBU) and 1,5-diazabicyclo[4.3.0]non-5-ene (DBN), and to mono-$C_1$-$C_6$-alkyl-, di-$C_1$-$C_6$-alkyl- and tri-$C_1$-$C_6$-alkylamines, especially triethylamine and tert-butylamine. Among the organic phosphines, preference is given to trialkylphosphines and triarylphosphines, for example tri-n-butylphosphine and triphenylphosphine. The catalysts can of course also be used as mixtures, optionally in combination with tri-$C_1$-$C_6$-alkylammonium halides and copper salts, for example triphenylphosphine in combination with a tri-$C_1$-$C_6$-alkylammonium halide and a copper salt, e.g. copper(I) chloride, copper(I) bromide, copper(II) chloride or copper(II) sulfate.

As well as the aforementioned constituents, the two-component binder composition may comprise the additives customary therefor. The choice of suitable conventional additives for the composition of the invention depends on the particular end use of the two-component binder composition and can be determined in the individual case by the person skilled in the art.

Suitable additives comprise, for example, antioxidants, UV absorbers/light stabilizers, metal deactivators, antistats, reinforcers, fillers, antifogging agents, blowing agents, biocides, plasticizers, lubricants, emulsifiers, colorants, pigments, rheology agents, impact tougheners, adhesion regulators, optical brighteners, flame retardants, antidripping agents, nucleating agents, wetting agents, thickeners, protective colloids, defoamers, tackifiers, solvents and reactive diluents, and mixtures thereof.

Fillers may be organic and inorganic in nature; preferred inorganic fillers take the form of platelets which can be aligned to form layers having enhanced barrier action against liquids and gases. Examples are sheet silicates such as montmorillonite and hectorite, as described, for example, in WO 2011/089089, WO 2012/175427 or in WO 2012/175431. Preference is given to sheet silicates having an aspect ratio of at least 50, at least 400, or at least 1000, and especially greater than or equal to 10 000. The layer thickness is, for example, about 1 nm. The sheet silicates may be of natural or synthetic origin. Suitable sheet silicates are, for example, montmorillonite, bentonite, kaolinite, mica, hectorite, fluorohectorite, saponite, beidellite, nontronite, stevensite, vermiculite, fluorovermiculite, halloysite, volkonskoite, suconite, magadite, sauconite, stibensite, stipulgite, attapulgite, illite, kenyaite, smectite, allevardite, muscovite, palygorskite, sepiolite, silinaite, grumantite, revdite, zeolite, fuller's earth, natural or synthetic talc or mica, or permutite. Particular preference is given to montmorillonite (aluminum magnesium silicate), hectorite (magnesium lithium silicate), synthetic fluorohectorite and exfoliated, organically modified smectites. The sheet silicates may be modified or unmodified. Preference is given to cationically modified sheet silicates. "Cationically modified" means that inorganic cations in the sheet silicate have been at least partly exchanged for organic cations, for example by an ion exchange method. Organic cations are organic compounds having at least one cationic group, for example quaternary ammonium group, phosphonium group, pyridinium group or the like, or a cationic amine salt.

Any light stabilizers/UV absorbers, antioxidants and metal deactivators used preferably have a high migration stability and thermal stability. They are selected, for example, from groups a) to t). The compounds of groups a) to g) and i) are light stabilizers/UV absorbers, while compounds j) to t) act as stabilizers.

a) 4,4-diarylbutadienes,
b) cinnamic esters,
c) benzotriazoles,
d) hydroxybenzophenones,
e) diphenyl cyanoacrylates,
f) oxamides,
g) 2-phenyl-1,3,5-triazines,
h) antioxidants,
i) nickel compounds,
j) sterically hindered amines,
k) metal deactivators,
l) phosphites and phosphonites,
m) hydroxylamines,
n) nitrones,
o) amine oxides,
p) benzofuranones and indolinones,
q) thio synergists,
r) peroxide-destroying compounds,
s) polyamide stabilizers and
t) basic costabilizers.

The two-component binder is preferably free of isocyanates, meaning that it preferably does not comprise any isocyanate compounds as hardeners. The two-component binder is preferably either in the form of a solution in an organic solvent or is solvent-free. "Solvent-free" means that less than 5% by weight, more preferably less than 2% by weight or zero organic solvent or water is present.

The two-component binder of the invention is capable of building up high binding forces even at room temperature within a short time and especially with amine hardeners.

EXAMPLES

Example 1: Synthesis of an Exovinylene Cyclocarbonate Dimethyl Acetal

The preparation is effected in two stages.

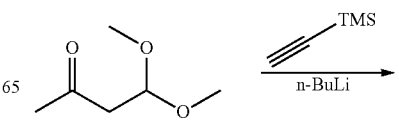

-continued

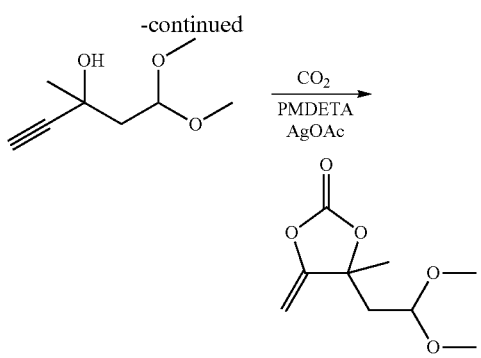

1.) Ethynylation of 4,4-dimethoxybutan-2-one:
TMS-acetylene (982 g, 10 mol) is initially charged under argon in THF (17 L, dried over molecular sieve) and cooled down to −68° C. While stirring, within 1 h, n-butyllithium (2.5 M in hexane, 4 L) is added dropwise at −68° C. and stirred for a further 1 h. Within 30 min, the ketone (1.319 kg, 10 mol) is then added dropwise at −68° C. to −54° C. and the mixture is subsequently stirred for a further 15 min. Thereafter, the mixture is warmed to 9° C. and water (2.9 L) is added in one portion. The temperature rises to about 17° C. The reaction mixture is concentrated thoroughly at 45° C./8 Torr. By GC analysis, it is ensured that no TMS-protected product is present any longer. The residue is suspended in diethyl ether (750 mL) and filtered, and the filtration residue is washed once again with diethyl ether. The filtrate is concentrated under reduced pressure. About 1.2 kg of raw material remain as a brown liquid. By vacuum distillation (5 mbar), about 1.1 kg (7 mol, 70%) of ethynylated product are obtained therefrom at 64-68° C. as a colorless oil.
Purity: >96% (GC area %)
2.) Ring Closure with $CO_2$:
The acetylene alcohol obtained in stage 1 (1233 g; 7.79 mol) is initially charged in acetonitrile (1.2 L) and, in a stirred autoclave, PMDETA (pentamethyldiethylenetriamine; 138.9 g; 0.8 mol) and AgOAc (12.9 g; 0.078 mol) are added. $CO_2$ is injected to 50 bar and the mixture is stirred for 2.5 h. The temperature rises up to 75° C. After cooling to room temperature, the reaction mixture is decompressed to standard pressure, filtered and concentrated at 100° C./5 mbar. About 1.5 kg of raw material remain as a brown liquid. By vacuum distillation at 5 mbar, about 1.39 kg of the carbonate are obtained therefrom at 114-115° C. as an orange oil which crystallizes through overnight (possibly after addition of a few seed crystals).
The mass of crystals is stirred with cyclohexane (1.34 L) and filtered with suction, and the residue is washed once again with cyclohexane (0.45 L). After drying under reduced pressure, 1.29 kg (6.38 mol, 64%) of almost colorless solids are obtained.
Purity: >99% (GC area %)

Example 2: Transacetalization with Hexane-1,6-Diol

In a 3-neck flask with stirrer, thermometer and vacuum connection, 30 g of the compound from example 1, 22.8 g of hexane-1,6-diol, 0.5 g of p-toluenesulfonic acid were suspended in 30 g of acetonitrile and heated to 45° C. Reduced pressure was applied and the solvent was distilled off, distilling at 45° C. for a total of 8 h and at room temperature for 40 h. This was followed by washing 3 times with 150 ml of demineralized water and decanting-off, and drying under reduced pressure.
Yield: 40 g of yellow viscous liquid
Zero-shear viscosity at 23° C.: 2 Pa s Example 3: Transacetalization with Butane-1,4-Diol In a 3-neck flask with stirrer, thermometer and vacuum connection, 100 g of the compound from example 1, 57.9 g of butane-1,4-diol were dissolved in 50 g of acetonitrile. 1.5 g of p-toluenesulfonic acid were dissolved in 10 g of acetonitrile and added to the mixture. The solvent was distilled off and vacuum was applied at room temperature for 40 h and distillation was continued at 45° C. for 8 h. This was followed by washing 3 times with 50 ml of demineralized water and decanting-off, and drying under reduced pressure.
Yield: 100 g of brown viscous liquid Example 4: Transacetalization with Triethylene Glycol In a 3-neck flask with stirrer, thermometer and vacuum connection, 100 g of the compound from example 1, 96.5 g of triethylene glycol (dried over molecular sieve), 1.36 g of p-toluenesulfonic acid were suspended in 50 g of acetonitrile and heated to 45° C. Reduced pressure was applied and the solvent was distilled off, and distillation was continued at 45° C. for 8 h and at room temperature for 40 h. This was followed by washing 3 times with 150 ml of demineralized water and decanting-off, and drying under reduced pressure.
Yield: 153 g of brown viscous liquid Example 5: Transacetalization with Hexane-1,6-Diol (Buffered, Dried Workup)

In a 3-neck flask with stirrer, thermometer and vacuum connection, 100 g of the compound from example 1, 75.98 g of hexane-1,6-diol, 1.7 g of p-toluenesulfonic acid were suspended in 100 g of acetonitrile and heated to 45° C. Reduced pressure was applied and the solvent was distilled off, distilling at 45° C. for a total of 8 h and at room temperature for 12 h. Then the product was taken up in 200 g of methyl tert-butyl ether, washed 3 times with 50 ml of pH7 buffer solution, dried with MgSO4 and filtered, and the solvent was removed by rotary evaporation.
Yield: 131 g of yellow viscous liquid Example 6: Transacetalization with Hexane-1,6-Diol (with Heterogeneous Catalyst)

In a 3-neck flask with stirrer, thermometer and vacuum connection, 20 g of the compound from example 1, 15.2 g of hexane-1,6-diol, 2.5 g of Amberlyst 15 dry, acidic (Sigma-Aldrich) were suspended in 20 ml of acetonitrile and heated to 45° C. Reduced pressure was applied and the solvent was distilled off, distilling at 45° C. for a total of 8 h and at room temperature for 40 h. Then the product was taken up in 100 g of methyl tert-butyl ether (MTBE), the heterogeneous catalyst was filtered off and the solvent was removed by rotary evaporation.
Yield: 19 g of brown viscous liquid Example 7: Transacetalization with Poly-THF In a 3-neck flask with stirrer, thermometer and vacuum connection, 20 g of the compound from example 1, 32 g of poly-THF 250, 0.34 g of p-toluenesulfonic acid were dissolved in 20 g of acetonitrile and heated to 45° C. Reduced pressure was applied and the solvent was distilled off, distilling at 45° C. for a total of 8 h and at room temperature for 40 h. Then the product was taken up in 100 g of methyl tert-butyl ether, washed 3 times with 50 ml of pH7 buffer solution, dried with MgSO4 and filtered, and the solvent was removed by rotary evaporation.

Yield: 37 g of yellow viscous liquid

Example 8: Transacetalization with 3-Methylpentanediol

In a 3-neck flask with stirrer, thermometer and vacuum connection, 50 g of the compound from example 1, 38 g of 3-methylpentane-1,5-diol, 0.85 g of p-toluenesulfonic acid were suspended in 50 g of acetonitrile and heated to 45° C. Reduced pressure was applied and the solvent was distilled off, distilling at 45° C. for a total of 8 h and at room temperature for 12 h. Then the product was taken up in 100 g of methyl tert-butyl ether, washed 3 times with 50 ml of pH7 buffer solution, dried with MgSO4 and filtered, and the solvent was removed by rotary evaporation.

Yield: 50.5 g of yellow viscous liquid
Zero-shear viscosity at 23° C.: 40 Pa s

Example 9: Transacetalization with Cyclohexane-1,6-Dimethanol

In a 3-neck flask with stirrer, thermometer and vacuum connection, 20 g of the compound from example 1, 18.5 g of cyclohexane-1,6-dimethanol, 0.34 g of p-toluenesulfonic acid were suspended in 20 g of acetonitrile and heated to 45° C. Reduced pressure was applied and the solvent was distilled off, distilling at 45° C. for a total of 8 h and at room temperature for 12 h. Then the product was taken up in 100 g of methyl tert-butyl ether, washed 3 times with 50 ml of pH7 buffer solution, dried with MgSO4 and filtered, and the solvent was removed by rotary evaporation.

Yield: 27 g of yellow, highly viscous liquid
Zero-shear viscosity at 23° C.: 425 Pa s Example 10: Transacetalization with Butanediol in Methanol In a 3-neck flask with stirrer, thermometer and vacuum connection, 30 g of the compound from example 1, 17.4 g of butane-1,4-diol were dissolved in 30 g of methanol. 0.51 g of methanesulfonic acid was dissolved in 10 g of methanol and added to the mixture. The solvent was distilled off and vacuum was applied at room temperature for 40 h and distillation was continued at 45° C. for 8 h. This was followed by washing 3 times with 150 ml of cold demineralized water and 3 times with 150 ml of warm demineralized water, which was decanted off, and drying under reduced pressure.

Yield: 14 g of brown viscous liquid

Example 11: Transacetalization with Octane-1,8-Diol

In a 3-neck flask with stirrer, thermometer and vacuum connection, 300 g of the compound from example 1, 282 g of octane-1,8-diol, 2.5 g of p-toluenesulfonic acid were suspended in 410 g of acetonitrile and then heated to external temperature 55° C. Reduced pressure was applied and the solvent was distilled off, in the course of which the internal temperature was not to fall below 50° C. (total of 8 h). Then vacuum was applied at room temperature for 15 h and degassing was effected once again at external temperature 50° C. for 8 h. Then the product was taken up in 400 g of methyl tert-butyl ether, washed 3 times with 150 ml of pH7 buffer solution, dried with MgSO4 and filtered, and the solvent was removed by rotary evaporation.

Yield: 457 g of red-brown viscous liquid
Zero-shear viscosity at 23° C.: 14 Pa s Example 12: Transacetalization with Diglycerol In a 3-neck flask with stirrer, thermometer and vacuum connection, 300 g of the compound from example 1, 123.3 g of diglycerol (CAS. No 59113-36-9 Inovyn) were dissolved in 100 g of methanol. 2.5 g of p-toluenesulfonic acid were dissolved in 10 g of methanol and added to the mixture. The solvent was distilled off and the mixture was distilled at room temperature for 8 h. This was followed by extractive stirring with 150 ml of pH 8 buffer solution, and the product was taken up in 300 ml of ethyl acetate, extracted by shaking twice with 150 ml of pH 7 buffer solution, dried with MgSO4, and the solvent was distilled off.

Yield: 298 g of very dark, very viscous liquid
Zero-shear viscosity at 23° C.: 4298 Pa s Example 13 (Comparison): Transacetalization with a Hydroxyalkyl Acrylate Copolymer (Acrylate Polymer as Connecting Group)

In a 3-neck flask with stirrer, thermometer and vacuum connection, 7 g of the compound from example 1 were dissolved together with 22.8 g of a hydroxyalkyl acrylate copolymer having an OH number of 85 mg KOH/g (Joncryl® 960, BASF) in 10 g of acetonitrile. 0.07 g of methanesulfonic acid was dissolved in 5 g of acetonitrile and added to the mixture. The solvent was distilled off and vacuum was applied at room temperature for 48 h until no OH band was visible any longer in the IR spectrum. The product is very highly viscous and hardly stirrable any more. This was followed by washing 3 times with 50 ml of demineralized water and decanting-off, and drying under reduced pressure.

Yield: 20 g of yellow, very viscous gel, no longer stirrable

Two-Component Coating Compositions 10 g of the product described in example 3 were blended with 2.0 g of the diamine 4,9-dioxadodecane-1,12-diamine (DODA) as hardener, and the resulting reactive two-component coating composition, immediately after mixing, was applied in a layer thickness of 3 μm to a printed 36 μm-thick polyester film. Then, in a calender, a second 36 μm-thick polyester film was laminated onto the coating layer under a pressure of 6.5 bar at a calendering speed of 5 m/min. The resulting laminate was cut into strips of width 15 mm and the peel strength of these strips was ascertained at room temperature (23° C.) after 4 h [N/15 mm]. This was done using a tensile testing machine, and the peel strength test was conducted at a peel angle of 90° (T-peel test). The results are shown in table 1.

Analogously, 10 g of the product described in example 5 were blended with 3.15 g of DODA as hardener, and processed and examined.

TABLE 1

Results of the peel test measurements

| | Peel strength after 4 h [N/15 mm] |
|---|---|
| 10 g of example 3 blended with 2 g of DODA | 3.2 |
| 10 g of example 5 blended with 3.15 g of DODA | 1.6 |

A peel strength of greater than 1 N after 4 h is sufficient for applications of the coating composition, for example for production of flexible packings, and builds up within a sufficiently short time to be industrially utilizable.

The invention claimed is:

1. A compound having two or more exovinylene cyclocarbonate units, where the exovinylene cyclocarbonate units are joined to one another via at least one organic, siloxane-free connecting group, wherein the connecting group is not bonded directly to the exovinylene double bonds and connecting groups formed by polymerization of (meth)acrylic monomers are excluded, and wherein, if the compound has exactly two exovinylene cyclocarbonate units, the connecting group has at least one acetal group.

2. The compound according to claim 1, wherein the exovinylene cyclocarbonate units are 5-vinylidene-1,3-dioxolan-2-one units of the formula (I):

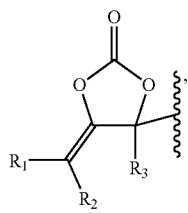

wherein:
the at least one organic, siloxane-free connecting group is between the 4 positions of the 5-vinylidene-1,3-dioxolan-2-one units; and
$R_1$ to $R_3$ are each independently hydrogen or an organic radical.

3. The compound according to claim 1, wherein the connecting group has at least one acetal group.

4. The compound according to claim 1, which has the formula (II):

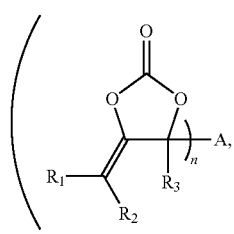

wherein:
$R_1$ to $R_3$ are independently hydrogen or an organic radical;
n is a number not less than 2; and
A is a siloxane-free organic connecting group, excluding a connecting group formed by polymerization of (meth)acrylic monomers;
or which has the formula (III):

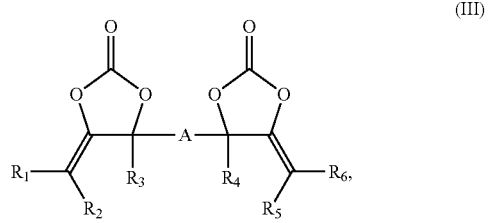

wherein:
$R_1$ to $R_6$ are independently hydrogen or an organic radical; and
A is a siloxane-free organic connecting group, excluding a connecting group formed by polymerization of (meth)acrylic monomers;
or which has the formula (IV):

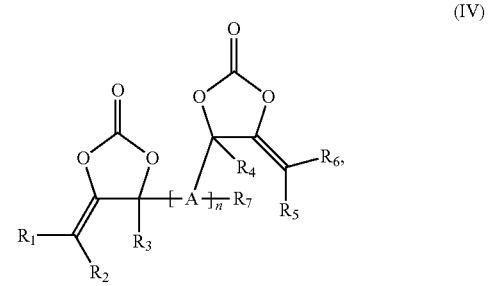

wherein:
$R_1$ to $R_6$ are independently hydrogen or an organic radical,
$R_7$ is hydrogen, an OH group or an organic radical,
A is a siloxane-free organic connecting group, excluding a connecting group formed by polymerization of (meth)acrylic monomers, and
n is a number not less than 1;
or which has the formula (V):

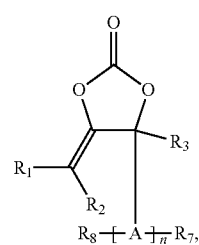

wherein:
$R_1$ to $R_3$ are independently hydrogen or an organic radical,
$R_7$ and $R_8$ are independently hydrogen, an OH group or an organic radical and $R_7$ and/or $R_8$ optionally comprise an exovinylene cyclocarbonate group,
A is a siloxane-free organic connecting group, excluding a connecting group formed by polymerization of (meth)acrylic monomers, and n is a number not less than 1, if at least one of the $R_7$ and $R_8$ radicals comprises at least one exovinylene cyclocarbonate group, and n is a number not less than 2, if $R_7$ and $R_8$ radicals do not comprise an exovinylene cyclocarbonate group.

5. The compound according to claim 4, wherein A has at least one acetal group.

6. The compound according to claim 4, wherein:

in the formula (II), -A is defined as —B-Q;

in the formula (III), -A- is defined as —B-Q-B—;

the compound is a compound of the formula (IVa):

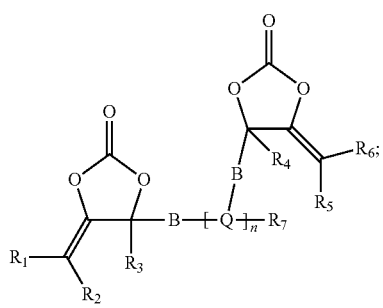

(IVa)

the compound is a compound of the formula (Va):

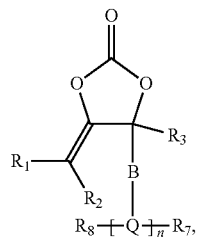

(Va)

wherein:

$R_1$ to $R_6$ are independently hydrogen or an organic radical, $R_7$ and $R_8$ are independently hydrogen, an OH group or an organic radical, B in each case is a divalent hydrocarbyl group, Q in each case is an organic radical; and n in the formula (IVa) is a number not less than 1; and in the formula (Va) is a number not less than 1, if at least one of the $R_7$ and $R_8$ radicals comprises at least one exovinylene cyclocarbonate group, and n is a number not less than 2, if the $R_7$ and $R_8$ radicals do not comprise an exovinylene cyclocarbonate group.

7. The compound according to claim 4, wherein:

$R_1$, $R_2$, $R_5$ and $R_6$ are independently a C1- to C10-alkyl group; and $R_3$ and $R_4$ are independently a C1 to C10 alkyl group or a hydrogen atom.

8. The compound according to claim 4, which is a compound of the formula (Vb):

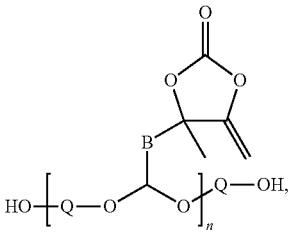

(Vb)

or of the formula (Vc):

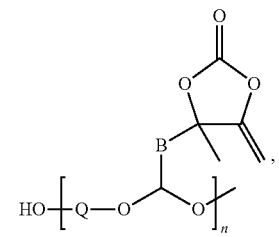

(Vc)

or of the formula (IVb):

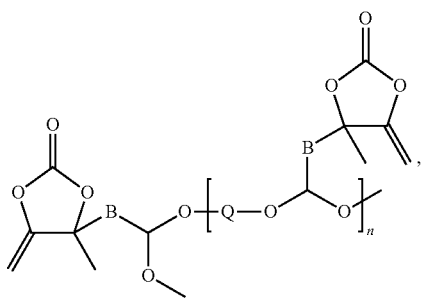

(IVb)

or of the formula (VI):

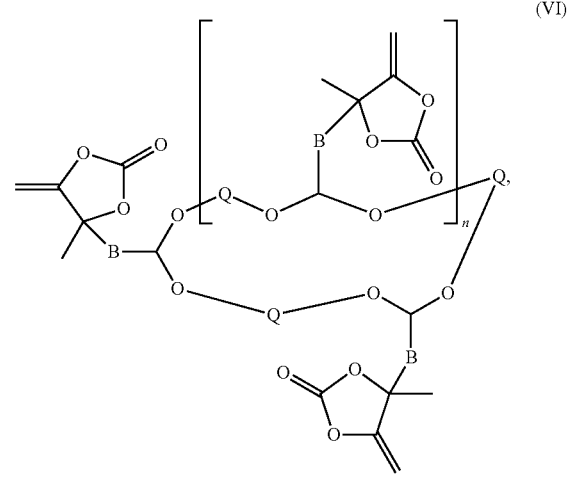

(VI)

wherein:
B is an alkylene group;
Q is a group derived from a polyol, a polyol being an alcohol having at least two hydroxyl groups;
n in the formulae (Vb) and (Vc) is a number not less than 2,
n in the formula (IVb) is a number not less than 1, and
n in the formula (VI) is a number not less than 0.

9. The compound according to claim 4, which is a compound of the formula (VIa):

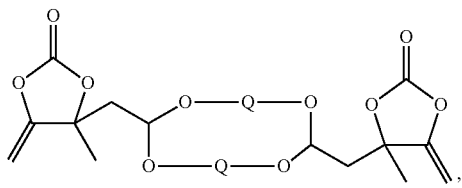
(VIa)

or of the formula (IVc):

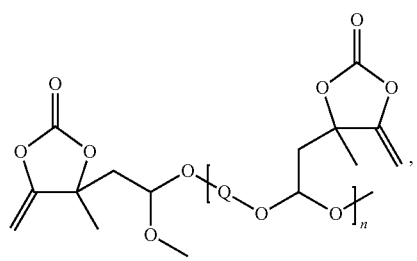
(IVc)

or of the formula (Vd):

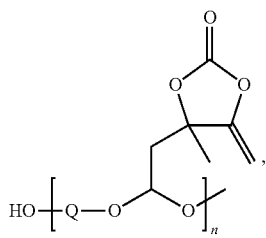
(Vd)

or of the formula (Ve):

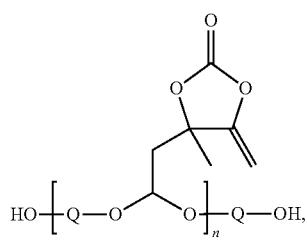
(Ve)

wherein:
—O-Q-O— in the formulae VIa, IVc, Vd and Ve is in each case the radical of a divalent alcohol, n in the formula (IVc) is 1, 2 or 3, and n in the formulae (Vd) and (Ve) is a number not less than 2.

10. The compound according to claim 4, wherein:
$R_1$, $R_2$, $R_5$ and $R_6$ are each a hydrogen atom;
$R_3$ and $R_4$ are independently methyl or a hydrogen atom; and
$R_7$, $R_8$ and A are independently radicals of polyhydric alcohols having 2 to 12 carbon atoms that are optionally interrupted by a —O—, —S— or —NR$_2$— group, wherein R is H or C1- to C12-alkyl.

11. The compound according to claim 1, which is prepared by transacetalization of an exovinylene cyclocarbonate of the formula (VII):

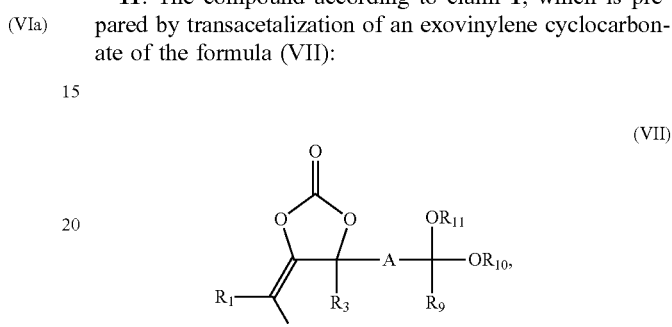
(VII)

wherein:
$R_1$ to $R_3$ and $R_9$ are independently hydrogen or an organic radical,
$R_{10}$ and $R_{11}$ are independently an organic radical, and
A is an organic connecting group.

12. The compound according to claim 11, wherein:
$R_1$ and $R_2$ are each a hydrogen atom;
$R_3$ and $R_9$ are independently methyl or a hydrogen atom,
$R_{10}$ and $R_{11}$ are independently alkyl groups having 1 to 4 carbon atoms, and
A is an alkylene group having 1 to 4 carbon atoms.

13. A process for preparing the compound according to claim 1, comprising reacting a compound having an exovinylene cyclocarbonate unit and at least one acetal group with at least one compound selected from the group consisting of a diol and a polyol.

14. The process according to claim 13, wherein the reacting occurs under catalysis by at least one Lewis acid or by at least one protic acid.

15. A reaction product obtained by the process of claim 13.

16. A binder for a varnish, paint, ink, building material, elastomer, foam, fiber or particle, the binder comprising a two-component composition comprising:
a first component comprising at least one compound of claim 1; and
a second component comprising at least one polyfunctional hardener having at least two functional groups selected from the group consisting of a primary amino group, secondary amino group, hydroxyl group, phosphine group, phosphonate group and mercaptan group.

17. The binder according to claim 16, wherein the two-component composition comprises at least one catalyst for catalyzing the reacting the exovinylene cyclocarbonate groups with the functional groups of the hardener.

18. A composition, comprising the compound according to claim 1, wherein the composition is at least one selected from the group consisting of a coating composition, varnish, paint, ink, building material, elastomer and foam.

* * * * *

UNITED STATES PATENT AND TRADEMARK OFFICE
CERTIFICATE OF CORRECTION

PATENT NO. : 10,604,500 B2
APPLICATION NO. : 16/335153
DATED : March 31, 2020
INVENTOR(S) : Ulrike Licht et al.

It is certified that error appears in the above-identified patent and that said Letters Patent is hereby corrected as shown below:

In the Claims

Column 26, Line 18, Claim 4, "$R_b$" should read -- $R_6$ --.

Signed and Sealed this
First Day of September, 2020

Andrei Iancu
*Director of the United States Patent and Trademark Office*